US006936016B2

(12) United States Patent
Berme et al.

(10) Patent No.: US 6,936,016 B2
(45) Date of Patent: Aug. 30, 2005

(54) METHOD FOR ANALYSIS OF ABNORMAL BODY TREMORS

(75) Inventors: Necip Berme, Worthington, OH (US); Hasan Cenk Guler, Columbus, OH (US)

(73) Assignee: Bertec Corporation, Columbus, OH (US)

( * ) Notice: Subject to any disclaimer, the term of this patent is extended or adjusted under 35 U.S.C. 154(b) by 497 days.

(21) Appl. No.: 10/151,213

(22) Filed: May 17, 2002

(65) Prior Publication Data

US 2003/0216656 A1 Nov. 20, 2003

(51) Int. Cl.⁷ .............................................. A61B 5/103

(52) U.S. Cl. ....................................... 600/595; 600/509

(58) Field of Search ................................ 600/587, 595, 600/509, 527, 508, 483, 513; 128/898

(56) References Cited

U.S. PATENT DOCUMENTS

| 2,680,438 | A | * | 6/1954 | Edwards ...................... 600/527 |
| 4,195,643 | A | | 4/1980 | Pratt, Jr. |
| 4,595,023 | A | | 6/1986 | Bonnet |
| 5,265,619 | A | | 11/1993 | Comby et al. |
| 5,293,879 | A | | 3/1994 | Vonk et al. |
| 5,620,003 | A | | 4/1997 | Sepponen |
| 6,030,347 | A | | 2/2000 | Nakamura et al. |

OTHER PUBLICATIONS http://www.indiana.edu hperk500/gcma01a/—Shriners Hospitals 6th annual gait and clinical movement analysis meeting website—abstracts. Apr. 16, 2001.*
Hallet M. 1998 "Overview of Human Tremor Physiology", *Movement Disorders*, vol. 13, suppl. 3, pp. 43–48.

Wade P., Gresty M.A. and Findley L.J., 1982. "A Normative Study of the Postural Tremor of the Hand". *Archives of Neurology*, vol. 39, pp. 358–362.
Gallasch E. and Kenner T., 1997. "Characterization of Arm Microvibration Recorded on an Accelerometer", *European Journal of Applied Physiology*, vol. 75, pp. 226–232.
Bircher M., Kohl J., Nigg B. and Koller E.A., 1978. "The Microvibration of the Body, an Index for Examination Stress", *European Journal Applied Physiology*, vol. 39, pp. 99–109.
Seliktar R., Susak Z., Najenson T. and Solzi P., 1978. "Dynamic Features of Standing and their Correlation with Neurological Disorders", *Scandinavian Journal of Rehabilitation Medicine* vol. 10, pp. 59–64.

(Continued)

*Primary Examiner*—Mark Bockelman
(74) *Attorney, Agent, or Firm*—Francis T. Kremblas, Jr.; Kremblas, Foster, Phillips & Pollick

(57) ABSTRACT

A method useful for evaluating abnormal body tremors wherein a subject is positioned onto a support surface and one or more components of the load exerted by the subject upon the support surface are measured. Simultaneously, the cardiac activity of the subject is also recorded and the time interval between each consecutive heartbeat is computed. The measured load output is modified to normalize the weight of the subject and then plotted against a modified frequency wherein each time interval between heartbeats represent a unit of time and a selected equal number of force measurement samples are interpolated between each heartbeat. The frequency spectrum analysis of such a modified power spectrum graph yields information about body tremor which can be compared to a prior analysis of the same subject or to the same analysis of a standard. The standard is created using the identical method upon, preferably, a sufficient number of subjects known to be free of abnormal body tremor to yield an average measure useful for comparison and diagnostic purposes.

5 Claims, 6 Drawing Sheets

OTHER PUBLICATIONS

Sturm R., Nigg B. and Koller E.A., 1980. "The Impact of Cardiac Activity on Triaxially Recorded Endogenous Microvibrations of the Body", *European Journal Applied Physiology*, vol. 44, pp. 83–96.

Koller E.A., Studer R., Gerber H. and Stussi E., 1986. "The Effect of Propranolol on Whole–Body Microvibrations during examination stress", *European Journal Applied Physiology* vol. 55, pp. 307–314.

Welch P.D., 1967, "The use of Fast Fourier Transform for the Estimation of Power Spectra: a Method based on Time Averaging over Short, Modified Periodograms", *IEEE Transactions on Audio and Electroacoustics*, vol. AU–15, pp. 70–73.

Oppenheim A.V. and Schafer R.W., "Discrete–time Signal Processing" Prentice Hall. Englewood Cliffs, New Jersey 1989.

Pagnacco, G., Oggero, E., Moor D.R., and Berme N., 1998 "Oversampling Data Acquistion to Improve REsolution of Digitized Signals" Biomedial Science Instrumentation, vol. 34, pp. 137–142.

* cited by examiner

METHOD FOR ANALYSIS OF ABNORMAL BODY TREMORS

CROSS-REFERENCE TO RELATED APPLICATIONS (Not applicable)

STATEMENT REGARDING FEDERALLY SPONSORED RESEARCH OR DEVELOPMENT (Not Applicable)

REFERENCE TO A "MICROFICHE APPENDIX"

(Not Applicable)

BACKGROUND OF THE INVENTION

1. Field of Invention

The present invention relates generally to methods and means for evaluating body tremors so as to distinguish tremors due to pathological conditions from non-pathological conditions.

2. Background of Related Art

Monitoring the physiological body tremor of humans or animals is an attractive idea as far as the neurological pathologies are concerned. A method which is non-invasive and relatively easy to perform for screening and detection of disorders at an early stage of development is desirable.

Different types of human body tremor result from a variety of mechanisms that include peripheral and central loops and central oscillators. In general, the sources of tremor may be classified as mechanical, reflex and central oscillator (Hallet, 1998)[1]. The mechanical tremor results from the inertial and stiffness characteristics of the human joints, whereas the reflex tremor originates from the peripheral and central reflex loops of the nervous system. The central regions of the nervous system may undergo spontaneous oscillations and send out rhythmic motor commands, which could lead to physiological termor of the human body.

Abnormalities in the physiological tremor may appear due to different pathologies of the nervous system. Essential tremor results from a central oscillator and has a frequency range of 8–12 Hz. Several types of tremors can be observed in patients with Parkinson's disease, but the most characteristic one is the tremor that is present at rest. It has a characteristic frequency between 3–7 Hz. Other very common types of tremor are the cerebellar, palatal, orthostatic, neuropathic and cortical tremors.

Several studies analyzed tremor in different parts of the body. Wade et al (1982)[2] measured tremor of the hand by placing an accelerometer on the dorsum of the hand. Amplitude and spectral characteristics of hand tremor were evaluated. In another study, Gallasch and Kenner (1997)[3] investigated the microvibration of the arm recorded with an accelerometer. The analysis was carried out during resting of the arm and gripping actions.

The measurement of the microvibrations of the body using a force plate date back to mid 70's. Bircher et al. (1978)[4] examined the effect of examination stress on the microvibrations of the human body that is quantified by measuring the rectified impulse using a force plate. The study also established a correlation between the vertical force during standing and cardiac output. In a different study, Seliktar et al. (1978)[5] tried to classify three different components of the ground reaction force during standing. A relatively higher frequency component was termed as "tremor" whereas an intermediate frequency component was designated as "ataxia". The lowest frequency constituent was labeled as "sway". Three different groups of subjects were tested: a control group, a group of patients with hemiplegia and a group of patients after severe craniocerebral injury. In a similar study, Strum et al. (1980)[6] evaluated the relationship between the cardiac activity and the microvibrations of the body. A force plate was used to assess the influence of the cardiac activity and muscle tone on the microvibrations under different test conditions. The effect of isoprenaline, exercise, cold stress and trunk flexion on microvibration was measured and compared to control subjects. The main conclusion was that the most important source of whole-body microvibration is the cardiac activity. Koller et al. (1986)[7] evaluated the effect of propranolol on whole-body microvibrations during examination stress. Similar to previous studies, the rectified impulse calculated using force plate data was used to assess microvibrations.

Prior to the present invention, the methods used to identify different types of body tremors required special equipment to be used such as exemplified in U.S. Pat. Nos. 4,595,023 and 5,265,619. A method using standard and readily commercially available components to measure and quantify body tremor would represent a significant advance over prior methods.

BRIEF SUMMARY OF THE DISCLOSURE

An object of the present invention is to provide a system and methodology to measure and quantify body tremor, which may be utilized to diagnose and/or monitor neurological disorders such as Parkinson's disease and Multiple Sclerosis, for example. Conventional equipment such as high-sensitivity force plates and electrocardiographs or other conventional devices for detecting cardio-activity may be used as basic components of the system.

Another aspect of the present invention is to identify signature characteristics of whole body tremor for normal subjects and/or for subjects with a known neurological disorder. These measurements would enable the development of a database for comparison with similar load measurements made using a subject suspected to have a disorder.

The present invention also may be used in the analysis of several other conditions that change the normal tremor characteristics of the body (e.g. stress, drug, tobacco or alcohol intake).

For a healthy person at rest, it is known that the major contribution to the microvibrations of the body is from cardiac activity. Analysis has shown that with a subject at rest on a force transducer, it is possible to identify each cardiac pulse resulting from a heartbeat using the measured force. The fact that the cardiac activity is a significant component of the measured force may also be confirmed using frequency analysis (see U.S. Pat. No. 4,195,643). Frequency spectrum analysis has confirmed that the force is composed of a periodic component at the frequency of the heartbeat and its higher harmonics. The spectrum also reveals the presence of side bands around the fundamental frequency (heartbeat) and the higher harmonics. These modulations can be proven to result from respiration activity of the subject. Consequently, these modulations introduce a contaminating effect, which degrades the spectrum in which the peaks are solely due to cardiac activity.

In the method according to the present invention the degrading effect of such modulations from the measured force is minimized to yield a clear spectrum that contains only information related to the heartbeats. As modified, a frequency spectrum analysis may used as the signature or standard for the body microvibrations of healthy subjects. Any abnormal variation in the body tremor of a single subject using this modified spectrum analysis would be revealed as a shift to a dominant frequency other than the heartbeat and its harmonics and/or as an increase in the spectral amplitude as compared to the determined standard. This altered or modified frequency spectrum analysis may be utilized to identify neurological disorders or effects of foreign substances, which may cause an abnormal tremor in the body.

In parallel to the analysis of the modified frequency distribution, the power content of measured and calculated variables, such as forces and point of force application, may also be used in distinguishing abnormal body tremor. In accordance with this aspect, the variance (or standard deviation) can be a representative quantity for the power content of the aforementioned variables.

Figure 1:
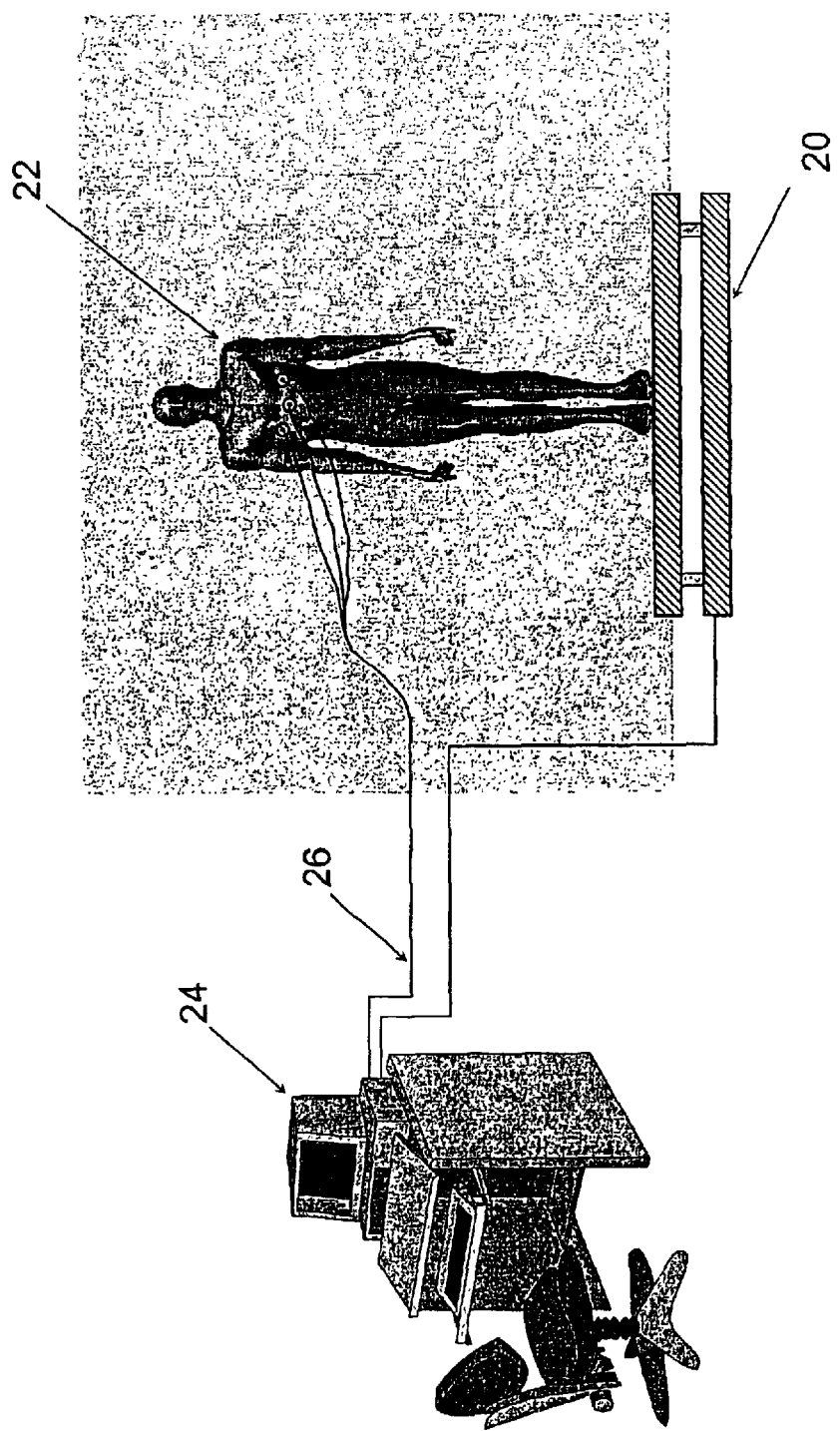
FIG. 1 is a diagrammatic view illustrating a body tremor analysis system constructed in accordance with the present invention.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose.

DETAILED DESCRIPTION OF THE INVENTION

This invention is related to the measurement of body microvibrations by making use of conventional load transducers and cardiac activity measurements in a method providing a relatively easy, quick, and non-invasive diagnostic procedure.

A general illustration of one preferred system is depicted in FIG. 1. The proposed system utilizes the principles of ballistocardiography to measure whole body microvibrations of a subject. It consists of at least one force plate provided with a force and/or moment transducer 20 with dimensions preferably large enough for a subject 22 disposed in a standing, sitting, or reclining position. Such force plate may be of conventional construction well-known to those skilled in the art. A simultaneous recording of the cardiac activity, such as by using an ECG device 26, is, carried out in parallel to the load measurements. A conventional computer 24 may be conventionally programmed to perform synchronous data acquisition and processing. The subject 22 may be disposed in a standing, sitting or reclining position on the force transducer. The components of the load exerted by the subject may be the vertical directed forces or the forces and moments related to the center of the applied pressure of the load.

For a person in good health without abnormal body tremor, the main component of whole body microvibrations originates from the activity of the heart. The inertial forces due to the beating heart and the pulsatile flow of blood in main arteries give rise to very small vibrations of the whole body at the frequency of the cardiac activity. The major component of these vibrations is along the long axis of the body. To demonstrate a preferred method of the present invention, a force plate provided with a strain gage based force transducer of high-sensitivity is used to detect the forces due to these vibrations. Preferably, the resolution of the transducer utilized to measure the microvibrations is less than about plus or minus 0.3 N. A three-lead conventional electrocardiography device is used to quantify the cardiac activity. As the essential information needed from cardiac activity is the time interval between consecutive repetitive heartbeat events corresponding to heartbeats, any means ranging from conventional electrocardiography to devices sensing the pressure changes at the subject's finger could be used.

Preferably data collection should be at least at 25 Hz to prevent aliasing of the signal since the frequency interval of interest lies below 10 Hz. It is also possible to utilize an oversampling procedure as described by Pagnacco et al. (1998)[10] in order to reduce the effect of quantization noise, if the data acquisition system does not have the desired resolution. The data collection period should preferably be long enough to enable reliable averaging of the collected data, if desired, for spectral analysis (Welch, 1967)[8]. Appropriate detrending and zero padding procedures may also be used if deemed appropriate and desirable.

Preferably, data should be filtered using a digital filter with a cutoff frequency of 10 Hz to remove measurement noise. The frequency analysis of the signals can be carried out in a number of different ways suitable for the application; see Oppenheim and Schafer, 1989[9]. One conventional method would be the Fast Fourier Transform technique. The selection of the type of the force transducer may depend on a trade-off between different factors such as cost, accuracy, resolution and power consumption. Such choices are within the level of one of ordinary skill in this art. Devices based on strain gages, piezoelectric of piezoresistive transducers or other conventional force transducers may also be employed to measure forces without departing from the present invention.

Figure 2:
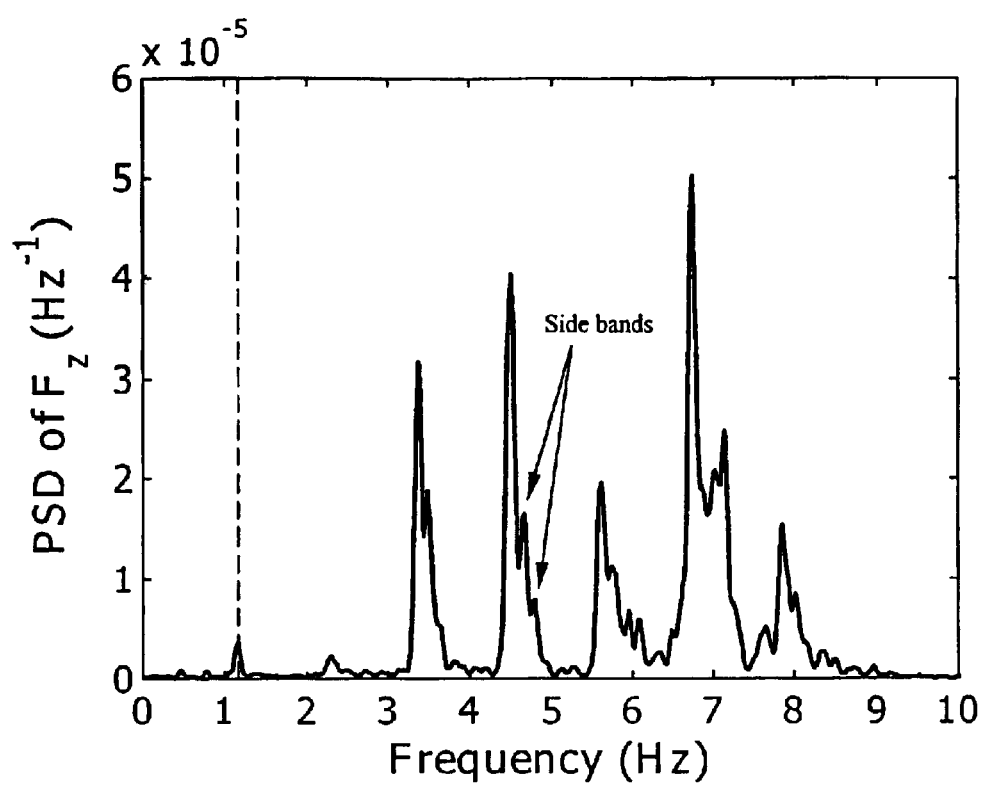
FIG. 2 illustrates a conventional power spectral density (PSD) of a measured vertical force of a subject while standing still on a force transducer platform such as shown in FIG. 1.
Figure 3:
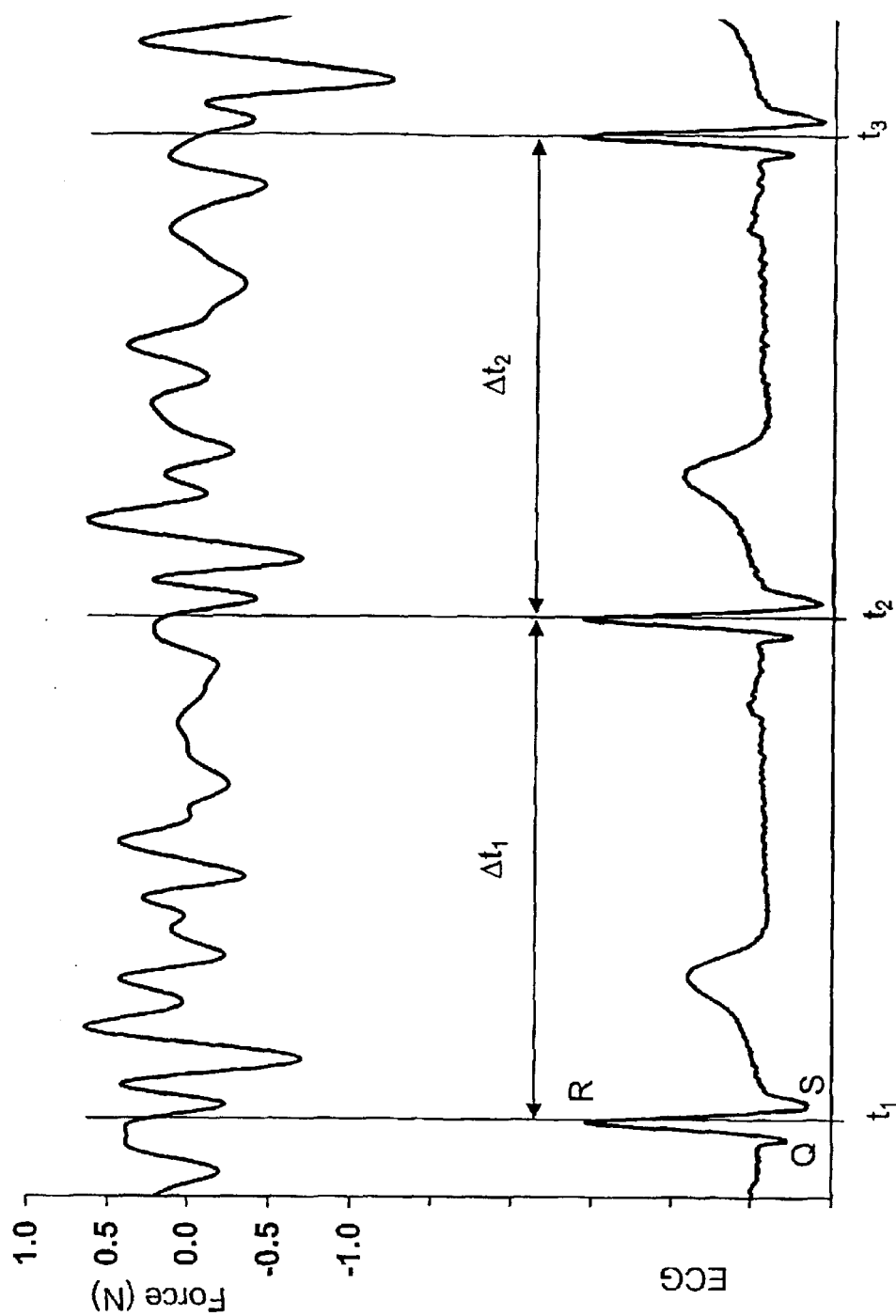
FIG. 3 is a sample of a synchronous record of an ECG reading and the measured vertical forces of a subject disposed upon a force platform.
Figure 4:
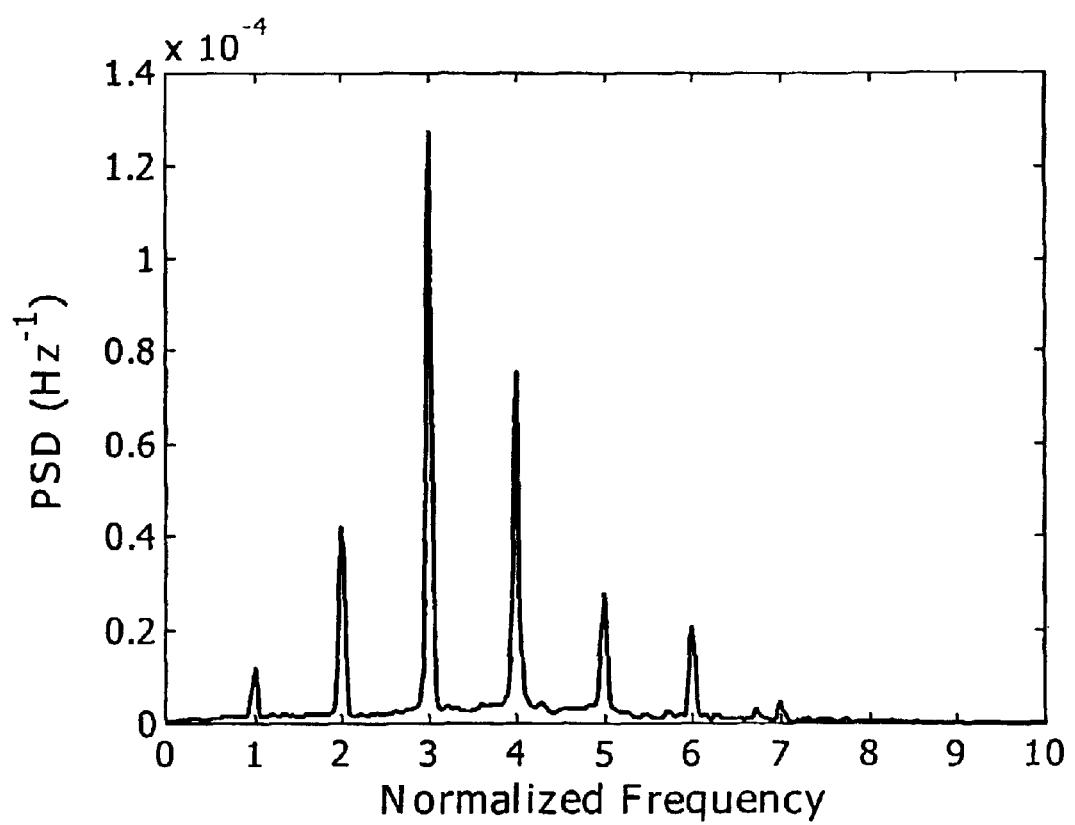
FIG. 4 is a graph of the PSD of frequency modified vertical force measurements averaged through 12 subjects in accordance with the present invention.
Figure 5:
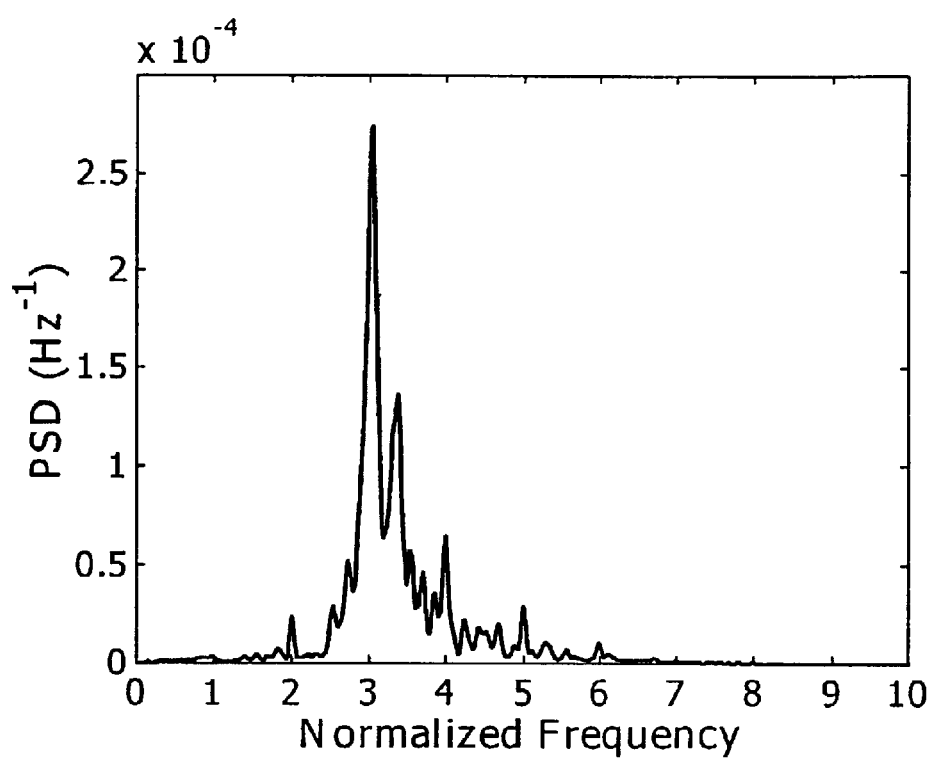
FIG. 5 is a graph of the PSD of frequency modified force measurements according to the present invention for a subject emulating a typical hand tremor.

FIG. 2 shows a typical power spectral density plot of the vertical force ($F_z$) computed using Fast Fourier Transform. This force is measured with a force plate while the subject is standing still. Before calculating the power spectral density, the vertical force is conventionally normalized with respect to the weight of the subject to eliminate body weight as a variable and the mean value is set to zero to remove the DC component of the spectrum. Peaks are observed at the heartbeat frequency (1.15 Hz for this particular subject) and its higher harmonics (2.3 Hz, 3.45 Hz). The relative amplitude of peaks may change from subject to subject. This plot also depicts clear side bands around the peaks, which differ from the higher harmonic peaks by integer multiples of the respiration frequency (0.15 Hz). These side bands indicate a strong modulation with respiration. These modulations are due to the regulatory effect of the respiration on the inter-beat intervals of the heartbeat. To be exact, the time interval between consecutive heartbeats is typically not constant and modulates at the respiration frequency. These modulations introduce a contaminating effect to the frequency distribution of the vertical force in the form of side bands. In accordance with the present invention the effect of respiration is eliminated and the power spectral density plot for different subjects is standardized by preforming a frequency modification procedure. First, the time instances for each heartbeat event (the QRS peaks in case of electrocardiograph, see FIG. 3) are determined ($t_1$, $t_2$ and $t_3$ illustrated in FIG. 3). Then, the vertical force time series is modified using interpolation such that it has an equal number of force samples distributed equally between each heartbeat event (i.e. QRS peak). This normalization or standardization procedure has the effect of introducing a modified time axis using the heartbeat events corresponding to the heartbeat as a time clock, which substantially eliminates any modulations due to respiration activity between heartbeat event intervals. FIG. 4, is an example of a power spectrum of the modified vertical forces determined in accordance with the present invention and averaged through testing 12 normal subjects known to be without any neurological tremor disorder. After performing the modification as described, the normalized or modified frequency axis has the unit of "heartbeats". This frequency-modified power spectrum from a group of normal subjects, such as shown in FIG. 4, can be utilized as a standard to quantify body tremor and detect abnormalities in other tested subjects. FIG. 5 shows the frequency normalized or modified power spectral density plot employing the method of the present invention for a subject emulating a very slight hand tremor. This hand tremor caused an increase in the power content around 3 Hz and changed relative amplitudes of the peaks when compared to FIG. 4.

This analysis using the frequency modified technique described is not limited to the vertical component of the ground reaction force. It can be equally applied to the horizontal force components, moment values and coordinates of center of pressure, for example.

The tremor measurements are not limited to a subject standing on the force plate. The same measurements can also be performed while the subject is reclining or sitting on a rigid support. The modified procedure described with respect to the heartbeat frequency enables one to make meaningful comparisons between subjects. Different methods for analysis of the spectral amplitudes are also possible. One such method may be dividing the spectral amplitudes by the variance of the force time series, which will normalize or standardize the area under the power spectral density curve to one. However, the absolute values of the peaks in the frequency distribution curve depend on the parameters used in calculating the spectrum (e.g. periodogram window width, or percentage of overlap between windows). The amplitude and width of the peaks are bound to change dependent upon the choice of these parameters.

Figure 6:
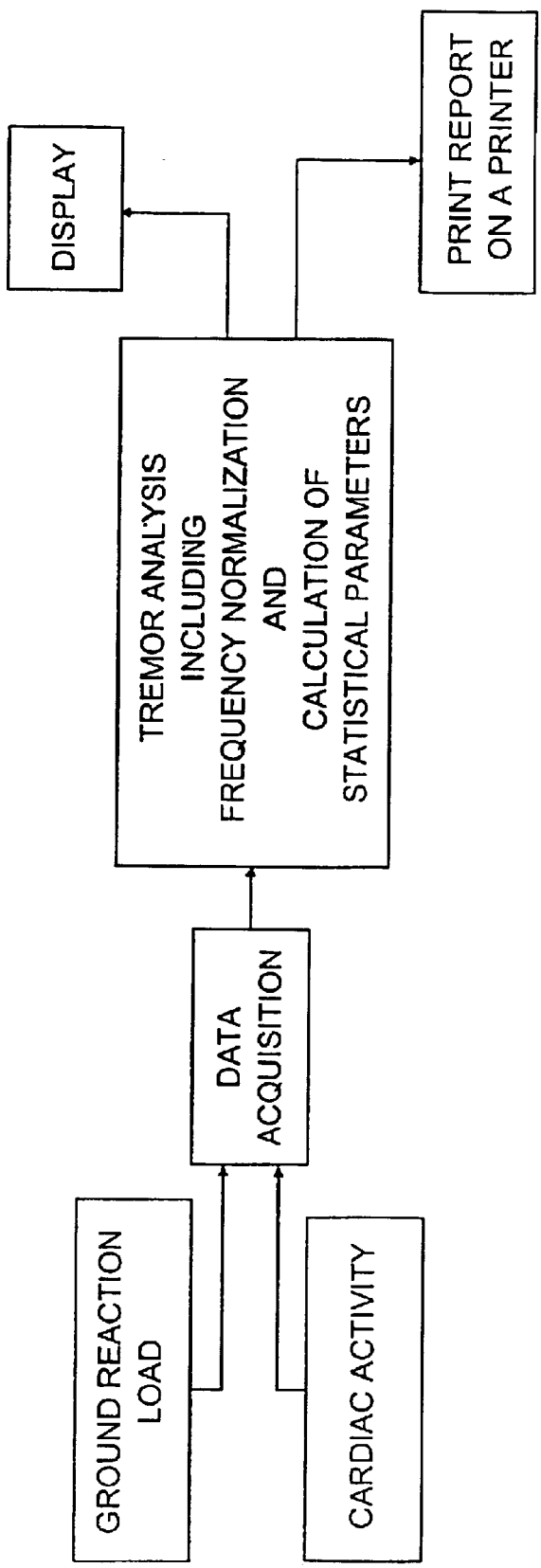
FIG. 6 is a block diagram of a preferred system for analysis of the whole body microvibrations according to the present invention and for preparation of a report for a tested subject, such as shown in FIG. 1.

The present invention may be implemented using conventional hardware, which includes appropriate data collection and analysis means as illustrated in FIG. 6. The entire algorithm may be on a single Erasable Programmable Read Only Memory chip. The output may be a liquid crystal display, which will present the power spectrum plot, and several other numerical parameters, if desired, such as statistical quantities related to the measured force and cardiac activity. An optional output may be to a printer, which will print a report for the analysis.

The following is a list of the references identified in the foregoing description:
1. Hallet M. 1998. "Overview of human tremor physiology", Movement Disorders, vol. 13, suppl. 3, pp. 43–48.
2. Wade P., Gresty M. A. and Findley L. J., 1982. "A normative study of the postural tremor of the hand", Archives of Neurology, vol. 39, pp. 358–362.
3. Gallasch E. and Kenner T., '997. "Characterization of arm microvibration recorded on an accelerometer", European Journal of Applied Physiology, vol. 75, pp. 226–232.
4. Bircher M., Kohl J., Nigg B. and Koller E. A., 1978. "The microvibration of the body, an index for examination stress", European Journal Applied Physiology, vol. 39, pp. 99–109.
5. Seliktar R., Susak Z., Najenson T. and Solzi P., 1978. "Dynamic features of standing and their correlation with neurological disorders", Scandinavian Journal of Rehabilitation Medicine, vol. 10, pp. 59–64.
6. Strum R., Nigg B. and Koller E. A., 1980. "The impact of cardiac activity on triaxially recorded endogenous microvibrations of the body", European Journal Applied Physiology, vol. 44, pp. 83–96.
7. Koller E. A., Studer R., Gerber H. and Stussi E., 1986. "The effect of propranolol on whole-body microvibrations during examination stress", European Journal Applied Physiology, vol. 55, pp. 307–314.
8. Welch P. D., 1967. "The use of fast fourier transform for the estimation of power spectra: a method based on time averaging over short, modified periodograms", IEEE Transactions on Audio and Electroacoustics, vol. AU-15, pp. 70–73.
9. Oppenheim A. V. and Schafer R. W. "Discrete-time signal processing", Prentice Hall, Englewood Cliffs, N.J., 1989.
10. Pagnacco, G., Oggero, E., Moor D. R., and Berme, N., 1998, "Oversampling Data Acquisition to Improve Resolution of Digitized Signals", Biomedical Sciences Instrumentation, Vol. 34, pp 137–142.

While certain preferred embodiments of the present invention have been disclosed in detail, it is to be understood that various modifications may be adopted without departing from the spirit of the invention or scope of the following claims.

What is claimed is:

1. A method for evaluating body tremor comprising the steps of:
    a) measuring one or more selected components of the load exerted by a human subject upon a support surface and simultaneously determining the time interval between each of a selected number of consecutive heartbeat events corresponding to each heartbeat of the subject;
    b) computing a modified frequency distribution of the load components measured in step (a) by interpolation of selected samples of said measurements wherein the samples of the measurements of the selected components made step (a) are equally spaced within each time interval determined in step (a) and of equal number from one interval to the next regardless of the heart rate of the subject being evaluated to minimize the effect of heart beat modulation of the subject upon the frequency distribution computed.

2. The method defined in claim 1 further comprising performing the identical steps on a selected number of human subjects known to be free of any significant abnormal body tremor and computing a modified frequency distribution representing an average of the one or more components of the load generated by each of the subjects to determine a modified frequency distribution standard and comparing said standard to a similar modified frequency distribution obtained performing the method of claim 1 upon a selected subject for body tremor diagnostic purposes.

3. The method defined in claim 1 wherein heartbeat events recorded represent the QRS peaks obtained using an electrocardiograph device.

4. The method defined in claim 1 wherein the heartbeat events recorded represent the blood pressure peak during each heartbeat.

5. The method defined in claim 1 wherein the components of the load measured are those forces exerted in a vertical direction relative to said support surface.

* * * * *